United States Patent [19]

Mia

[11] Patent Number: 4,608,251

[45] Date of Patent: Aug. 26, 1986

[54] LHRH ANALOGUES USEFUL IN STIMULATING ANTI-LHRH ANTIBODIES AND VACCINES CONTAINING SUCH ANALOGUES

[75] Inventor: Abdus S. Mia, Fairless Hills, Pa.

[73] Assignee: Pitman-Moore, Inc., Washington Crossing, N.J.

[21] Appl. No.: 670,469

[22] Filed: Nov. 9, 1984

[51] Int. Cl.$^4$ .................. A61K 39/395; A61K 37/24; C07K 7/06

[52] U.S. Cl. ........................................ 424/85; 424/88; 514/2; 514/19; 514/800; 530/313; 530/328

[58] Field of Search .............. 260/112.5 R, 112.5 LH, 260/112 B, 112 R; 424/85, 88; 514/2, 19, 800

[56] References Cited

U.S. PATENT DOCUMENTS

| | | | |
|---|---|---|---|
| 3,963,691 | 6/1976 | Hoffman et al. | 260/112.5 LH |
| 4,377,574 | 3/1983 | Rivier et al. | 424/177 |
| 4,478,744 | 10/1984 | Mezei et al. | 260/112.5 R |
| 4,481,190 | 11/1984 | Nestor et al. | 424/177 |
| 4,489,061 | 12/1984 | Rivier et al. | 424/177 |

OTHER PUBLICATIONS

Seprodi et al, Branched–Chain Analogues of LHRH, *J. Med. Chem.*, vol. 21(3) 1978, p. 276.
Myer et al, Protein–Peptide Conjugation by Two-–Phase Reaction, *Biochem. J.*, vol. 227(1) 1985, p. 343.
CA #26022s, vol. 100, 1983, Conjugates of Haptene and Muranyl Peptides . . . Activity, Audilient.
Abstract, The 64th Conf. of Research Workers in Animal Disease, Monday, Nov. 14—Tuesday, Nov. 15, 1983, Americana Congress, Michigan at Congress, Chicago, "A Synthetic Antifertility Vaccine for Animals".
Abstract, The 64th Conf. of Research Workers in Animal Disease, Monday, Nov. 14—Tuesday, Nov. 15, 1983, Americana Congress, Michigan at Congress, Chicago, "Production of Monoclonal Antibody Against Luteinizing Hormone Releasing Hormone (LHRH)".
"Production of Antiserum to LH–Releasing Hormone (LH–RH) Associated with Gonadal Atrophy in Rabbits: Development of Radioimmunoassays for LH–RH", No. 5, Arimura et al., Endo., vol. 93, pp. 1092–1103, (1973).
"Effect of Active Immunization to Luteinizing Hormone Releasing Hormone on Serum and Pituitary Gonadotrophins, Testes and Accessory Sex Organs in the Male Rat", Fraser et al., J. Endocr. (1974), vol. 63, No. 2, pp. 399–406.
"Preparation and Specificity of Antibodies to the Decapeptide, Luteinizing Hormone–Releasing Hormone (LH–RH)", Jeffcoate et al., Immunochemistry, 1974, vol. 11, pp. 75–77.
"Active Immunization of Ewes Against Luteinizing Hormone Releasing Hormone, and Its Effects on Ovulation and Gonadotrophin, Prolactin and Ovarian Steroid Secretion", J. Endocr. (1978), vol. 78, pp. 39–47.
"Specificity of Anti-LH-RH Antisera Induced by Different Immunogens", Pique, et al., Immunochemistry, (1978), vol. 15, pp. 55–60.
"Preparation and Formulation of a Human Chorionic Gonadotropin Antifertility Vaccine: Selection of a Peptide Immunogen", Stevens et al., American Journal of Reproductive Immunology, (1981), vol. 1, pp. 307–314.

*Primary Examiner*—Blondel Hazel
*Assistant Examiner*—Garnette D. Draper
*Attorney, Agent, or Firm*—David J. Levy

[57] ABSTRACT

A conjugate between a nona- or decapeptide of the formula (i) or (ii):

$$\text{Lys-Trp-Ser-Tyr-Gly-Leu-Arg-Pro-Gly-NH}_2, \qquad (i)$$

or $$\text{Cys-Lys-Trp-Ser-Try-Gly-Leu-Arg-Pro-Gly-NH}_2, \qquad (ii)$$

or mixtures of peptides (i) and (ii).

and a protein is provided which, when used per se or when mixed with a suitable adjuvant, yields a vaccine which acts as an immunogen for LHRH and induces a mammal to produce antibodies which react with LHRH. Immunization against the body's LRHR results in lowering of male and female sex hormones including luteinizing hormone so as to prevent conception. Other uses for materials which lessen the effect of LHRH in the body are known in the art.

29 Claims, No Drawings

LHRH ANALOGUES USEFUL IN STIMULATING ANTI-LHRH ANTIBODIES AND VACCINES CONTAINING SUCH ANALOGUES

BACKGROUND OF THE INVENTION

Luteinizing Hormone Releasing Hormone ("LHRH") is secreted by the hypothalamus and carried to the pituitary gland where it stimulates secretion of follicle stimulating hormone and luteinizing hormone which, in turn stimulate ovarian follicle development, the conversion of ovarian follicle to corpus luteum, tubule development in the testicles and production of progesterone and testosterone. Thus, release of LHRH causes ovulation and formation of corpus luteum in females and spermatogenesis in males.

LHRH is a decapeptide of the following structure:

pGlu-His-Trp-Ser-Tyr-Gly-Leu-Arg-Pro-Gly-NH$_2$ wherein, according to convention, the amino group of each amino acid appears to the left and the carboxyl to the right with the hydroxyl of the carboxyl of the terminal Gly being replaced by an NH$_2$ group. The conventional abbreviations for the amino acids are: Glu (glutamic acid), pGlu (pyroglutamic acid), His (histidine), Trp (tryptophane), Ser (serine), Tyr (tyrosine), Gly (glycine), Leu (leucine), Arg (arginine), Pro (proline), Lys (lysine) and Cys (cysteine). Except for glycine which has no optical center, all amino acids are of the L-configuration unless otherwise indicated. LHRH may be produced as described in U.S. Pat. Nos. 4,159,980 and 4,213,895.

Analogues of LHRH have been prepared which act as agonists or antagonists of LHRH, i.e., which tend to diminish or accentuate the action of LHRH in the body. Such analogues are described in U.S. Pat. Nos. 3,880,825; 3,941,763; 4,034,082; 4,072,668; 4,075,192; 4,143,133; 4,143,136; 4,211,769; 4,234,571; and 4,263,282. These analogues may be administered to the animal or patient in amounts such as 2 to 200 micrograms per kilogram of body weight to yield an immediate effect on the reproductive cycle as described in U.S. Pat. No. 4,010,261. A second type of treatment is the administration to the patient or animal of an LHRH analogue as an antigen, i.e., immunogen, whereby the analogue acts as a vaccine and the host mammal generates antibodies to the analogue which also act against the body's own LHRH. Thus, the analogue's effect will persist after the analogue itself has been metabolized or excreted. This second treatment is described for various LHRH analogues or LHRH itself by A. Arimura et al. in Endocrinology 93:1092–1103 (1973); by H. M. Fraser et al. in the Journal of Endocrinology 63:399–406 (1974); by S. L. Jeffcoate et al. in Immunochemistry Vol. 11, p. 75–77 (1974); by I. J. Clarke et al. in the Journal of Endocrinology 78:39–47 (1978); by L. Pique et al. in Immunochemistry Vol. 15 pages 55–60 (1978); by V. C. Stevens et al. in the American Journal of Reproductive Immunology 1:307–314 (1981); and in U.S. Pat. No. 3,963,691.

An object of the present invention is a vaccine containing an immunogen which prevents the function of LHRH when administered to a male or female mammal. At present there are 43 million dogs and 31 million cats in the United States and their numbers increase daily. Stray dogs and cats along with wild animals such as skunks and raccoons are known to be major sources of rabies transmission to domestic animals and humans. Surgical removal of reproductive organs, e.g., spaying and castration, is presently a commonly used method for preventing reproduction in mammals. However, surgery is relatively costly, time consuming and impractical when used with wild or stray animals. A vaccine which immunizes the animal against its own LHRH would prevent conception for extended periods and would be a cost-effective method of population control. A further object is a vaccine form which can be used in dart-guns or drug-containing bullets for the immunization of wild mammals. An object of the invention is a vaccine for population control of a large population of animals such as deer, wild horses and burros and animals kept in zoos.

A further object of the invention is a vaccine containing an immunogen for the treatment of male mammals for the undesired effects of LHRH in such animals. For example, cryptorchidism is a condition where one or both testicles of a male mammal have not descended from the abdomen making castration a difficult surgical procedure. A vaccine which prevents LHRH from transmitting signals to produce male hormones would be, in effect, an "immunological castration" for male mammals and could be used to render cryptorchid stallions docile.

SUMMARY OF THE INVENTION

The invention comprises an immunogenic vaccine which contains the nonapeptide Lys-Trp-Ser-Tyr-Gly-Leu-Arg-Pro-Gly-NH$_2$ or the decapeptide Cys-Lys-Trp-Ser-Tyr-Gly-Leu-Arg-Pro-Gly-NH$_2$. When administered to a mammal, the vaccine induces in vivo production of antibodies to the host's LHRH whereby the natural secretion of LHRH is neutralized. The vaccine can be used to immunize the mammal against conception or any other conditions which are directly or indirectly influenced by secretion of LHRH. For example, the vaccine can be used in the treatment of prostate cancer in men.

DETAILED DESCRIPTION OF THE INVENTION

The vaccine of the invention contains as the immunological agent, a conjugate between a protein and a peptide selected from:

Lys-Trp-Ser-Tyr-Gly-Leu-Arg-Pro-Gly-NH$_2$,     (i)

or

Cys-Lys-Trp-Ser-Tyr-Gly-Leu-Arg-Pro-Gly-NH$_2$     (ii)

or mixtures of (i) and (ii). The vaccine can be administered as the conjugate per se in solid form as a lyophilized solid or may be micro- or macroencapsulated. Preferably, the vaccine is used as a liquid emulsion, most particularly as a water-in-oil emulsion with the conjugate in the aqueous phase. The emulsion may be described as an adjuvant, the protein as a carrier protein and the peptide as an LHRH analogue.

Peptides (i) and (ii) are written above using conventional abbreviations where the amino group of each amino acid appears to the left and the carboxyl group to the right. The last 8 amino acids of both compounds are the same and in the same order as the last 8 amino acids of LHRH. The individual amino acids making up peptides (i) and (ii) above and (iii) described below are preferably each of the L-configuration in view of their lower cost compared to the D-configuration. However, the invention comprises peptides wherein each or any of the amino acids are of the D-configuration. Peptides (i) and (ii) may be obtained from Peninsula Laboratories, Inc. of 611 Taylor Way, Belmont, CA 94002 or other commercial custom peptide synthesizers, including Bachem Inc. of 3132 Kashiwa Street, Torrance, CA 90505 and Vega Biochemicals of Tucson, Ariz. 85734. Further, they may be prepared by conventional methods known in the art such as by solid phase synthesis using benzhydrylamine resin, protected amino acids, a coupling reagent such as dicyclohexylcarbodiimide (DCC), removal of protecting groups with liquid hydrofluoric acid and purification by counter current distribution, $C_{18}$ column high pressure liquid chromatography and gel chromatography. Such techniques are described in the text by John Stewart and Janice Young entitled "Solid Phase Peptide Synthesis", W. H. Freeman & Co., San Francisco, 1969 and in U.S. Pat. No. 3,941,763. Benzhydrylamine resin may be prepared as described by P. Rivaille et al. in Helvetica Chimica Acta, Vol. 54 pages 2772-2775 (1971). Peptide synthesis may also be accomplished by solid phase synthesis and segment condensation synthesis as described in "The Proteins" Ed. by Hans Neuath et al., Vol 2, 3rd edition, Academic Press, N.Y. (1976) at pages 105-253 written by Frances M. Finn et al. and at pages 257-527 written by Bruce W. Erickson et al., respectively.

The carrier protein used in the invention is preferably one with a molecular weight of at least about 40,000 dalton and more preferably at least about 60,000 dalton. In a particular aspect of the invention, the protein may be of human origin such as to heighten the immune response when the vaccine is administered to an animal while rendering the vaccine less dangerous to a human if it is accidentally given to a human. Peptide (i) contains alpha- and epsilon-$NH_2$ groups for conjugation to the carrier protein. Except at very low pH, peptide (ii) dimerizes quickly through the SH groups of Cys to the peptide of the following formula (iii):

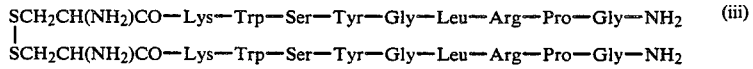

Formation of the dimer makes conjugation through the SH group uncertain. However, the disulfide-bonded dimer (iii) may conjugate to the carrier protein through either —$NH_2$ group to provide the advantage of 2 LHRH analogue determinants through one bond between an —$NH_2$ group of the analogue and one —COOH group of the carrier protein. Carrier proteins which may be used in the invention include albumin, such as from bovine, baboon, dog, chicken egg, turkey egg, goat, guinea pig, hamster, human, mouse, pigeon, porcine, rabbit, rat, sheep or other sources, immunoglobulin from such sources or hemocyanin such as from Keyhole Limpets such materials being available from Sigma Chemical of St. Louis, Mo. Keyhole Limpet Hemocyanin (KLH), e.g., as obtained from Cal Biochem of La Jolla, CA, is preferred in view of its high immunogenicity.

Conjugation between the peptide and the carrier protein may be carried out as described by J. H. Kennedy et al. in Clinica Chimica Acta, Vol. 70, pages 1-31 (1976) with conjugating agents such as glutaraldehyde or a water soluble carbodiimide, e.g., 1-(3-dimethylaminopropyl)-3-ethylcarbodiimide hydrochloride (ECDI).

The conjugate may be administered per se as a vaccine or preferably micro- or macroencapsulated. Alternatively, the conjugate is provided with an adjuvant for administration to the mammal. This is preferably a water-in-oil emulsion, it being found that an oil-in-water emulsion gives markedly inferior results. Thus, an aqueous solution of the peptide-protein conjugate of the invention is formulated into a stable water-in-oil emulsion using an oil phase consisting of an oil such as mineral oil and a non-ionic emulsifier. Suitable mineral oils include those having a viscosity of about 8 to 20 centistokes at 40° C., e.g., Drakeol 6 obtained from the Penreco Division of the Pennzoil Co. Nonionic emulsifier include Montanide 888 obtained from Seppic of 70 Champs Elyees, Paris, France. The non-ionic emulsifier may be used with the oil in a weight ration of about 1:6 to 1:12, e.g., about 1:9. For a water-in-oil emulsion, the aqueous phase is slowly added to the oil phase in a homogenizer after which the mixture is emulsified to yield an emulsion having a viscosity of about 200 to 400 centistokes at 40° C. Viscosity measurements may be taken on a Cannon-Ubbelohde Viscometer, available from Cannon Instruments Co. of State College, PA as described in U.S. Pat. No. 2,805,570. The thus-produced vaccine emulsion is stable for at least 1 month at 37° C.

The emulsion vaccine may be administered parenterally to a mammal. Vaccine in the liquid form, e.g., in a water-in-oil emulsion, may be injected by syringe. In the solid form, e.g., lyophilized conjugate, may be used in a ballistic implant or dart gun arrangement as described in U.S. Pat. Nos. 3,948,263 and 3,982,536 which are incorporated by reference. Such devices are available from BallisiVet Inc. of White Bear Lake, Minn. The amount of conjugate to be administered to the mammal to achieve production of anti-LHRH antibodies essentially equivalent to be host's production of LHRH will depend on the degree of conjugation between peptide and protein and the size and species of the host. In general, about 0.2 to 1.0 mg of conjugate per kilogram of body weight is administered and is given twice at a 3 to 6 week interval. Annual booster administrations of the same dose is recommended for a continued effect. Since the antibody titer will decrease gradually, the effect of the invention vaccine will diminish and is thus reversible, which is an advantage of the invention over prior surgical methods.

The vaccine of the invention, as described above, may be used to treat any condition in man or other mammals which is brought on or aggravated by LHRH. The vaccine is thus an effective contraceptive agent in males and females, an agent to treat sexual hyperactivity in males and females, e.g., for the treatment of cryptorchidism in male mammals such as horses, and the treatment of cancers and other conditions which are stimulated by sexual hormones. For example, cancer of the prostate gland is believed to be advanced by male hormones and removal of male gonads or injection of antagonistic female hormones is often used for treatment. The anti-LHRH vaccine of the invention may be used to treat prostate cancer by preventing LHRH from signaling the secretion of male hormones.

EXAMPLE 1

Preparation of Peptide (ii)

Synthesis of peptide (ii) was carried out by the solid phase method using para-metyylbenzhydrylamine resin with the protected amino acids, in order of coupling: Boc-Gly, Boc-Pro, Boc-Arg(Tos), Boc-Leu, Boc-Gly, Boc-Tyr(BrZ), Boc-Ser(OBzl), Boc-Trp, Boc-Lys(-ClZ) and Boc-Cys(MBzl). The coupling reagent was DCC (dicyclohexylcarbodiimide), Boc (butyloxycarbonyl) removal by trifluoroacetic acid and neutralization by triethylamine. After the synthesis on a Beckman Model 990 Synthesizer, the peptide was removed from the resin and all protecting groups by liquid HF. Purification was by counter current distribution and gel chromatography.

In more detail, the cycle of steps used for the addition of each amino acid is as follows, where washes are for one minute each, unless otherwise stated.

1. Methylene chloride, three times
2. 40% trifluoroacetic acid in methylene chloride, once for two minutes
3. 40% trifluoroacetic acid in methylene chloride, once for 25 minutes
4. Methylene chloride, once
5. Ethanol, once for two minutes
6. Methylene chloride, twice
7. 10% triethylamine in methylene chloride, once for two minutes
8. 10% triethylamine in methylene chloride, once for 10 minutes
9. Methylene chloride, three times After this series of washes, the appropriate amino acid derivative and dicyclohexylcarbodiimide are added at three-fold excess, and coupling to the growing peptide proceeds for the next two hours. The first amino acid residue is incorporated by coupling Boc-glycine to the benzhydrylamine styrene resin. Serine is added as the benzyl ester and cysteine as the S-methoxybenzyl derivative. Tyrosine is added as Boc-Tyr(Br-Z), arginine as Boc-Ar(os) and lysine as Boc-Lys(Cl-Z). After the peptide has been synthesized, it is given a final deprotection with trifluroacetic acid and is washed with methanol and dried. The peptide is removed from the dry resin with anhydrous hydrogen fluoride, using anisole to minimize side reactions. This reaction requires about 45 minutes at 0 degrees C. The resin is then dried under vacuum. The peptide-polystyrene mixture is washed with ether and the peptide is extracted with 10% acetic acid. The peptide solution is lyophilized to give the crude peptide. Three grams of crude peptide were applied in two lots to a countercurrent distribution apparatus, using the solvent system described below for peptide (i). Each run gave 0.9 grams of partially purified peptide. The 1.8 grams of peptide was applied to a large P-2 column in 10% acetic acid. The peptide was easily soluble in 10% acetic acid and the eluate was collected at 4 drops per second and 15 ml/tube. Tubes 27-35 contained 1.005 grams of pure peptide.

Preparation of Peptide (i)

Synthesis of peptide (i) was carried out as peptide (ii) above with protected amino acids, in order of coupling, Boc-Gly, Boc-Pro, Boc-Arg(Tos), Boc-leu, Boc-Gly, Boc-Tyr(Br-Z), Boc-Ser(OBzl), Boc-Trp and Boc-Lys(Z). Purification was by countercurrent distribution and $C_{18}$ column purification.

In more detail, peptide (i) was made by coupling the first amino acid, glycine, as Boc-glycine in BHA resin. From this point the synthesis of the crude peptide was as above, as was the HF cleavage. Three grams of the crude peptide were applied to a counter-current distribution apparatus using the solvent system 4:1:5 of butanol:acetic acid:water. Fractions 88 to 109 contained 0.9 grams of a partially purified peptide. These fractions were pooled and lyophilized. The partially purified peptide was applied to a C-18 column where the initial solvent was 0.1% acetic acid and the final solvent was 80% acetonitrile containing 0.1% acetic acid. A linear gradient was used with 700 ml of each solvent. Peptide fractions that appeared pure by TLC were pooled and submitted to quality control.

EXAMPLE 2

Peptide (i)-BSA Conjugate

Into 1 ml of 0.85% NaCl solution made with distilled water was dissolved 20 mg of bovine serum albumin (BSA). 10 mg of peptide (i) was dissolved in 1 ml of distilled water and slowly added to the BSA solution with constant mixing. 100 mg of 1-(3-dimethylaminopropyl)-3-ethylcarbodiimide hydrochloride (ECDI) was dissolved in 0.5 ml of distilled water and slowly added to the BSA solution with constant mixing. The mixture is then incubated for 6 hours at room temperature with constant stirring in a shaker. The mixture was then dialyzed against 2 to 3 liters of phosphate buffer saline (PBS) for about 16 to 24 hours at 5° C. The dialyzing process was repeated twice. The dialyzed conjugate was then filter sterilized and assayed for the degree of conjugation.

EXAMPLE 3

Peptide (i)-HSA Conjugate

The procedure of Example 2 was repeated substituting human serum albumin (HSA) for BSA to obtain a peptide (i)-HSA conjugate.

EXAMPLE 4

Peptide (i)-KLH Conjugate

An aqueous solution of about 1.5 to 2% Key Hole Limpet (KLH) was dialyzed against a 0.85% NaCl saline solution for about 36 to 48 hours with two changes of saline solution. The KLH solution protein concentration was then determined by the Biuret Reaction Method using a BSA standard. The Biuret method is described by A. G. Gornall et al. in the Journal of Biological Chemistry, Vol. 177, page 751 (1949). As determined by the Biuret method, 20 mg of KLH was then conjugated to 10 mg of peptide (i) as described in Example 2 to yield a peptide (i)-KLH conjugate.

EXAMPLE 5

Peptide (ii)-HSA Conjuqate

A conjugate of peptide (ii) and HSA was prepared by the method described in Example 3 substituting peptide (ii) for peptide (i).

EXAMPLE 6

Peptide (ii)-KLH Conjugate

The procedure of Example 4 was repeated substituting peptide (ii) for peptide (i) to obtain a conjugate between peptide (ii) and KLH.

EXAMPLE 7

Peptide (ii)-HgG Conjugate

Twenty mg of human gamma globulin (HgG) was dissolved in a mixture of 2 ml of PBS and about 0.25 ml of dimethylformamide into which had been dissolved 5 mg of m-maleimidobenzoyl-N-hydroxysuccinimide (MBS). The thus-produced mixture was allowed to react at room temperature for 25 minutes. The activated HgG was then separated from unreacted materials by adding PBS and subjecting the mixture to gel filtration on SEPHADEX® G 25 gel available from Sigma Chemical Co. of St. Louis, Mo. To the activated HgG in PBS was added 10 mg of peptide (ii) which was then incubated for 2 hours at room temperature. The mixture was dialyzed as in Example 2, filter sterilized and assayed for the degree of conjugation.

EXAMPLE 8

Determination of Degree of Conjugation

The degree of conjugation of peptide (i) or (ii) to the carrier protein in Examples 2-7 was estimated by the Biuret method. In this procedure, the total weight of protein in the unconjugated protein is determined along with the protein weight in the conjugate, after dialyzing the conjugate to remove any unconjugated peptide (i) or (ii). The difference in protein weight is the conjugated peptide and from this, the degree of conjugation of peptide to carrier protein can be determined.

Using the biuret technique, it was found that the degree of conjugation of the conjugates of Examples 2-7 was about 10 to 40 peptides per 100,000 dalton of molecular weight of the carrier protein.

EXAMPLES 9-14

Adjuvant Vaccines

The conjugates produced in Examples 2-7, respectively, were individually diluted with phosphate buffer saline (PBS) to make 5 to 15 mg/ml solutions. Thimerosal (1 part per 10,000 by volume) was added as a preservative and the material was sterilized either by filter sterilization, e.g., through a 0.2 μm disc, or by gamma irradiation. This constitutes the aqueous phase of the water-in-oil adjuvant vaccine. The oil phase was made by mixing 1 part of the nonionic emulsifer Montanide 888 with 9 parts of Drakeol 6 light white mineral oil followed by filter sterilization. The sterile oil phase is placed in the proper size emulsifying or homogenizing flask equipped with side tubelettes. A Virtis homogenizer Model 23 or 45 made by Virtis of Gardiner, N.Y. 12525 is started at low speed and an equal amount of the aqueous phase was added slowly. After the entire aqueous phase was added, the mixture was emulsified at a higher speed until an effective water in-oil emulsion was made.

The stability of the individual emulsions was determined by centrifuging a sample of the emulsion at 10,000 to 12,000 G for 6 minutes at which no more than 5% separation was detected. The viscosity of the preparation was typically between 260 to 300 centistokes per second. The emulsions were found to be stable for more than one month at 37° C.

EXAMPLE 15

Vaccine Efficacy—Rats

The vaccines produced in Examples 9-14 from the conjugate produced in Examples 2-7, respectively, were tested for blockage of the effects of LHRH in rats.

Young rats were inoculated intramuscularly with 1.0 ml, 0.5 ml and/or 0.2 ml of the vaccines produced in Examples 9-14 followed by a booster injection of the same dose, 3-4 weeks after the first injection.

Serum titer for antibody against LHRH was determined by the ELISA test as described by A. Voller et al. in the Bulletin of the World Health Organization, Vol. 53, pages 55-65 (1976) and in the "Manual of Clinical Immunology", Chapter 69, pages 506-512, American Society of Microbiology (1976). Microelisa plates were coated with synthetic LHRH. Antibody titers were determined at 4-6 weeks intervals.

In addition, the effectiveness of the vaccine was determined by observing the atrophy of the testicles in the case of males and the uterus and ovaries in the females. The results are shown in the following Table I.

TABLE I
RESULTS OF ANTIFERTILITY VACCINE

| Example | Conjugate | Dose | Antibody Titer Range | Gonadal Atrophy* |
|---------|-----------|------|---------------------|------------------|
| 9  | (i)-BSA   | 1.0 ml | 640-6400      | 7/7** |
| 10 | (i)-HSA   | 1.0 ml | <50-6400      | 3/4   |
| 10 | (i)-HSA   | 0.5 ml | 800-6400      | 3/4   |
| 10 | (i)-HSA   | 0.2 ml | 50-6400       | 0/5   |
| 11 | (i)-KLH   | 1.0 ml | >6400         | 4/4   |
| 11 | (i)-KLH   | 0.5 ml | 800-6400      | 3/3   |
| 11 | (i)-KLH   | 0.2 ml | 50-6400       | 5/5   |
| 12 | (ii)-HSA  | 1.0 ml | >6400         | 5/5   |
| 12 | (ii)-HSA  | 0.5 ml | 200->6400     | 2/5   |
| 12 | (ii)-HSA  | 0.2 ml | 1600->6400    | 3/5   |
| 13 | (ii)-KLH  | 1.0 ml | 400->6400     | 4/4   |
| 13 | (ii)-KLH  | 0.5 ml | 800->6400     | 4/4   |
| 13 | (ii)-KLH  | 0.2 ml | >50-6400      | 4/5   |
| 14 | (ii)-HgG  | 0.5 ml | 800-6400      | 4/5   |

*Atrophy is considered to be positive if the size has diminished to 75% or less of the control group.
**Number of vaccinated animals with positive atrophy/number vaccinated.

From the above data, the peptide (i)-KLH vaccine is considered to constitute the preferred embodiment of the invention.

EXAMPLE 16

Vaccine Efficacy—Cats

The vaccine produced in Example 11 was tested for efficacy in cats. Five female and three male cats were each given a 0.5 ml injection of the peptide (i)-KLH vaccine with a second 0.5 ml injection 4 weeks after the first. Immediately before the second injection, the anti-LHRH antibody titer range for the cats was found to be 800-1600 and 4 weeks after the second injection, the range was 12,800-51,200.

The female cats did not come into heat 18 months after the first injection even after being exposed to a normal male cat.

The male cats all had gonadal atrophy according to the atrophy definition in Example 15 for at least one year after the first injections. One male cat showed gonadal reversion to a normal size 18 months after the first injection.

EXAMPLE 17

Vaccine Efficacy—Horse

The vaccine produced in Example 10 was tested for efficacy against cryptorchidism in horses. A cryptorchid stallion was found to have a serum testosterone level of 0.7 nanograms per ml and an anti-LHRH antibody titer of 10 as determined by the ELISA test using LHRH as the antigen. The animal was injected with 3 ml of the peptide (i)-HSA vaccine produced in Example 10. A second injection of 3 ml of the vaccine was made 4 weeks after the first. Just prior to the second injection, the animal's serum testosterone level was found to be 0.09 nanograms per ml with an antibody titer of 2560. Four weeks after the second injection, these figures were found to be 0.05 and 20,480, respectively.

What is claimed is:

1. An immunogen vaccine which induces in a manmal production of antibodies against LHRH, which vaccine comprises a water in oil emulsion, the water phase comprising conjugate between a protein and a biologically effective amount of a peptide selected from the group consisting of:

Lys-Trp-Ser-Tyr-Gly-Leu-Arg-Pro-Gly-NH$_2$, or

Cys-Lys-Trp-Ser-Tyr-Gly-Leu-Arg-Pro-Gly-NH$_2$, or mixtures of

Lys-Trp-Ser-Tyr-Gly-Leu-Arg-Pro-Gly-NH$_2$, and

Cys-Lys-Trp-Ser-Tyr-Gly-Leu-Arg-Pro-Gly-NH$_2$.

2. The vaccine of claim 1, wherein said peptide is

Lys-Trp-Ser-Tyr-Gly-Leu-Arg-Pro-Gly-NH$_2$.

3. The vaccine of claim 1, wherein said peptide is

Cys-Lys-Trp-Ser-Tyr-Gly-Leu-Arg-Pro-Gly-NH$_2$.

4. The vaccine of claim 1, wherein said peptide is a mixture of

Lys-Trp-Ser-Tyr-Gly-Leu-Arg-Pro-Gly-NH$_2$, and

Cys-Lys-Trp-Ser-Tyr-Gly-Leu-Arg-Pro-Gly-NH$_2$.

5. The vaccine of claim 1, wherein the amino acids of said peptides are L-amino acids.

6. The vaccine of claim 1, wherein said protein has a molecular weight of at least about 40,000 dalton.

7. The vaccine of claim 1, wherein said peptide (ii) is present at least in part as a dimer.

8. The vaccine of claim 1, wherein said peptide is conjugated to said protein in a ratio of about 10 to 40 peptide molecules per 100,000 dalton molecular weight of the protein.

9. The vaccine of claim 1, wherein the oil phase further comprises a non-ionic emulsifier.

10. The vaccine of claim 1, wherein said water phase and said oil phase are present in said emulsion in approximately equal parts by volume.

11. A method of inducing in a mammal the production of antibodies to LHRH which comprises administering to the mammal an immunogen vaccine which induces in the mammal production of antibodies against LHRH, which vaccine comprises a water in oil emulsion, the water phase comprising a conjugate between a protein and a biologically effective amount of a peptide selected from the group consisting of:

Lys-Trp-Ser-Tyr-Gly-Leu-Arg-Pro-Gly-NH$_2$, or

Cys-Lys-Trp-Ser-Tyr-Gly-Leu-Arg-Pro-Gly-NH$_2$, or mixtures of

Lys-Trp-Ser-Tyr-Gly-Leu-Arg-Pro-Gly-NH$_2$, and

Cys-Lys-Trp-Ser-Tyr-Gly-Leu-Arg-Pro-Gly-NH$_2$.

12. The method of claim 11, wherein said vaccine is administered parenterally.

13. A method of preventing ovulation in a mammal which comprises administering to the mammal an immunogen vaccine which induces in the mammal Production of antibodies against LHRH, which vaccine comprises a water in oil emulsion, the water phase comprising a conjugate between a protein and a biologically effective amount of a peptide selected from the group consisting of:

Lys-Trp-Ser-Tyr-Gly-Leu-Arg-Pro-Gly-NH$_2$, or

Cys-Lys-Trp-Ser-Tyr-Gly-Leu-Arg-Pro-Gly-NH$_2$, or mixtures of

Lys-Trp-Ser-Tyr-Gly-Leu-Arg-Pro-Gly-NH$_2$, and

Cys-Lys-Trp-Ser-Tyr-Gly-Leu-Arg-Pro-Gly-NH$_2$.

14. The method of claim 13, wherein said mammal is a non-human mammal.

15. A method of treating a mammal for cryptorchidism which comprises administering to the mammal an immunogen vaccine which induces in the mammal production of antibodies against LHRH, which vaccine comprises a water in oil emulsion, the water phase comprising a conjugate between a protein and a biologically effective amount of a peptide selected from the group consisting of:

Lys-Trp-Ser-Tyr-Gly-Leu-Arg-Pro-Gly-NH$_2$, or

Cys-Lys-Trp-Ser-Tyr-Gly-Leu-Arg-Pro-Gly-NH$_2$, or mixtures of

Lys-Trp-Ser-Tyr-Gly-Leu-Arg-Pro-Gly-NH$_2$, and

Cys-Lys-Trp-Ser-Tyr-Gly-Leu-Arg-Pro-Gly-NH$_2$.

16. The method of claim 15, wherein said mammal is a stallion horse.

17. A peptide selected from the group consisting of:

Lys-Trp-Ser-Try-Gly-Leu-Arg-Pro-Gly-NH$_2$,

Cys-Lys-Trp-Ser-Tyr-Gly-Leu-Arg-Pro-Gly-NH$_2$, and

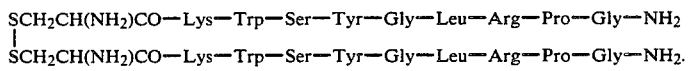

18. The peptide of claim 17, wherein said peptide is

Lys-Trp-Ser-Tyr-Gly-Leu-Arg-Pro-Gly-NH₂.

19. The peptide of claim 17, wherein said peptide is

Cys-Lys-Trp-Ser-Tyr-Gly-Leu-Arg-Pro-Gly-NH₂.

20. The peptide of claim 17, wherein said peptide is

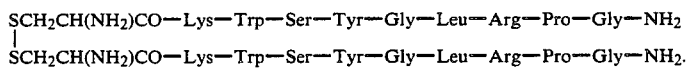

21. A conjugate between a protein having a molecular weight of at least about 40,000 and a peptide selected from the group consisting of:

Lys-Trp-Ser-Tyr-Gly-Leu-Arg-Pro-Gly-NH₂, or

Cys-Lys-Trp-Ser-Tyr-Gly-Leu-Arg-Pro-Gly-NH₂, or mixtures of

Lys-Trp-Ser-Tyr-Gly-Leu-Arg-Pro-Gly-NH₂, and

Cys-Lys-Trp-Ser-Tyr-Gly-Leu-Arg-Pro-Gly-NH₂.

22. The conjugate of claim 21, wherein said protein has a molecular weight of at least about 60,000 dalton.

23. The conjugate of claim 21, wherein said peptide is

Lys-Trp-Ser-Tyr-Gly-Leu-Arg-Pro-Gly-NH₂.

24. The conjugate of claim 21, wherein said peptide is

Cys-Lys-Trp-Ser-Tyr-Gly-Leu-Arg-Pro-Gly-NH₂.

25. The conjugate of claim 21, wherein said peptide is a mixture of

Lys-Trp-Ser-Tyr-Gly-Leu-Arg-Pro-Gly-NH₂, and

Cys-Lys-Trp-Ser-Tyr-Gly-Leu-Arg-Pro-Gly-NH₂.

26. The conjugate of claim 21, wherein said

Cys-Lys-Trp-Ser-Tyr-Gly-Leu-Arg-Pro-Gly-NH₂ is present at least in part as a dimer.

27. The conjugate of claim 21, wherein said protein is of human origin.

28. The conjugate of claim 21, wherein said protein is albumin, immunoglobulin or hemocyanin.

29. The conjugate of claim 28, wherein said protein is Keyhole Limpet Hemocyanin.

* * * * *